US007299949B2

(12) United States Patent
Greiner-Perth

(10) Patent No.: US 7,299,949 B2
(45) Date of Patent: Nov. 27, 2007

(54) DISCHARGE DEVICE FOR MANUALLY PRODUCING A VOLUME FLOW

(75) Inventor: Juergen Greiner-Perth, Gottmadingen (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 836 days.

(21) Appl. No.: 10/776,995

(22) Filed: Feb. 11, 2004

(65) Prior Publication Data

US 2004/0159679 A1 Aug. 19, 2004

(30) Foreign Application Priority Data

Feb. 12, 2003 (DE) ................................ 103 06 686

(51) Int. Cl.
*A61M 11/00* (2006.01)

(52) U.S. Cl. .................. 222/153.13; 222/82; 222/83.5; 222/320; 222/321.6; 222/384; 222/386

(58) Field of Classification Search ........... 222/153.11, 222/153.13, 153.14, 321.1, 81–83.5, 321.6, 222/309, 319, 320, 384, 386
See application file for complete search history.

(56) References Cited

U.S. PATENT DOCUMENTS

| | | | |
|---|---|---|---|
| 5,110,052 | A | 5/1992 | Graf et al. |
| 5,147,087 | A | 9/1992 | Fuchs |
| 5,307,953 | A | 5/1994 | Regan |
| 5,791,518 | A | 8/1998 | Amann et al. |
| 6,257,454 | B1 | 7/2001 | Ritsche |
| 6,257,457 | B1 | 7/2001 | Oechsel |

FOREIGN PATENT DOCUMENTS

| | | |
|---|---|---|
| DE | 4005527 | 8/1991 |
| DE | 4011537 | 10/1991 |
| DE | 4412041 | 10/1995 |
| DE | 4438375 | 5/1996 |
| DE | 19819748 | 11/1999 |
| EP | 0 546 607 A1 | 6/1993 |
| FR | 2 761 281 | 10/1998 |
| WO | WO 8900085 | 1/1989 |
| WO | WO 8900086 | 1/1989 |

OTHER PUBLICATIONS

European Patent Office Search Report dated Apr. 6, 2006 (4 pages).
German Patent Office Search Report dated Nov. 17, 2005 (3 pages).

*Primary Examiner*—J. Casimer Jacyna
(74) *Attorney, Agent, or Firm*—Flynn, Thiel, Boutell & Tanis, P.C.

(57) ABSTRACT

A discharge device for manually producing a volume flow by a discharge stroke, having a medium reservoir for at least one medium, a discharge opening, a pumping device and a working area associated with the pumping device and which in the inoperative position has a detachable, positive connection to a holding area by means of a locking device is known.

According to the invention the locking device in at least one plane orthogonal to a discharge stroke direction has an at least zonally or circumferentially corrugated and/or polygonal cross-section.

Use for discharging a medium.

17 Claims, 2 Drawing Sheets

DISCHARGE DEVICE FOR MANUALLY PRODUCING A VOLUME FLOW

BACKGROUND OF THE INVENTION

The invention relates to a discharge device for manually producing a volume flow by a discharge stroke, having a medium reservoir for at least one medium, a discharge opening, a pumping device and a working area associated with the pumping device, which working area in an inoperative position is provided by means of a locking device with a detachable, positive connection to a holding area.

Numerous different designs of such discharge devices are known from the prior art. A discharge of at least one medium, particularly a pulverized solid, a liquid with an aqueous to viscous consistency or a gas is of great significance in many cosmetic and pharmaceutical sectors. For this purpose at least one medium is stored in a medium reservoir of the discharge device and can be fed by means of a manually functioning pumping device through a discharge opening into the environment. The pumping device pressurizes the medium in the medium reservoir and thereby brings about the discharge of the medium through the discharge opening. The discharge opening is matched to the viscosity and area of application of the medium to be discharged. Particularly in the case of a medium with a limited particle size, aqueous consistency and low viscosity frequently an atomization in the ambient air is sought by using a nozzle-shaped discharge opening. For a highly viscous medium on the other hand more particularly a cylindrical or conical discharge opening is preferred.

For the discharge of the medium a working area is provided, which in an inoperative position is provided by means of a locking device with a detachable, positive connection to a holding area, the positive connection consequently preventing an undesired operation of the pumping device. In order to bring about the discharge of the medium, the user exerts an operating force on the discharge device, which leads to a relative movement between the holding area and the working area. However, this relative movement only becomes possible when the operating force exerted by the user on the discharge device exceeds a control force determined by the positive connection between the working area and the holding area. This releases the positive connection between the working area and the holding area. Subsequently the desired pressure build-up in the medium reservoir of the discharge device is brought about.

Discharge devices designed for a small number of pump strokes, particularly for one or two pump strokes, frequently have a sealed medium reservoir. For this purpose the pumping device is designed in such a way that the medium to be discharged is only fed out of the medium reservoir sealed up to this time directly during the performance of the pump stroke. The pumping device opens during said first pump stroke the seal of the medium reservoir and places the latter under pressure. Discharge devices designed for a small number of pump strokes are more particularly used for the administration of inoculating agents and/or other highly active medicaments. Since then only a one or two times operation of the pumping device is required and for hygienic reasons the discharge device must subsequently be disposed of, great interest is attached to a particularly inexpensive, but reliable discharge device.

When using such discharge devices for inoculating agents, which are particularly intended for use during epidemics or catastrophes and must therefore be storable over a long time period, account must be taken of ageing effects.

Ageing not only occurs with respect to the medium stored in the discharge device, but also with respect to the discharge device per se.

Discharge devices are in particular made from plastics material where, even in the case of optimum storage conditions, over a long period of time a change occurs to the material characteristics such as the material density, material volume, modulus of elasticity and notched bar impact strength. As a result of such an ageing of plastics material there can be a change to the control forces or a failure of the discharge device in use, so that doubts are cast on the application of the stored medium.

SUMMARY OF THE INVENTION

The object of the invention is to provide a discharge device of the aforementioned type, which minimizes the action on the discharge device of the ageing effects of the materials used.

This object is solved in that the locking device is provided in at least one plane and orthogonally to a discharge stroke direction with an at least zonally or circumferentially corrugated and/or polygonal cross-section. The discharge stroke direction is determined through the design of the working area and the holding area, which in particular must be matched in such a way that only a translatory degree of freedom of the movement is made possible for the pumping device. In a plane orthogonal to the discharge stroke direction the locking device is preferably designed in such a way that it has an at least zonally or preferably circumferentially corrugated cross-section. This cross-section can in particular be created by a continuous or discontinuous lining up of several arcuate segments, straight portions or combinations thereof. As a result of the rounded transitions of such a locking device design, there are additional manufacturing and strength advantages compared with an at least zonally, polygonal cross-section. In a preferred embodiment the locking device surrounds in particular in circular manner the cylindrically constructed working area and as a result of the corrugated cross-section it is possible to avoid a large-area engagement between the locking device and the working area. Instead the working area and locking device only come into contact with one another in punctiform and/or linear and/or a real manner. Thus, on operating the discharge device there is a readily predeterminable frictional resistance between the working area and the locking device. No significant modifications occur to the frictional resistance as a result of ageing effects, because as a result of the corrugated cross-section there can be a limitation to the normal force determining the frictional force. Thus, with such a locking device design and in conjunction with the working area, a long-term functionality of the discharge device is ensured.

According to a first embodiment of the invention on at least one locking device corrugated projection facing the working area is provided a locking element. A corrugated projection is more particularly a convex area of the locking device shaped by the zonally or circumferentially corrugated cross-section. The corrugated projection faces the working area and with respect to other areas of the locking device has a minimum spacing from the working area. A locking element constitutes a positive and/or non-positive connection between the locking device and the working area and is in particular constructed as a raised area, detent or catch nose. On the working area is provided at least one depression or protuberance, particularly a pocket, a groove, a collar or a web. The locking element is positively connected to said protuberance or depression, especially by engaging behind. An arrangement of the locking element on a corrugated projection facing the working area makes it possible to design the locking element as a compact and consequently highly loadable geometry on which only limited forces act during the discharge stroke. Thus, the function of the locking element can be ensured even in the case of ageing and embrittlement of the material.

According to a further embodiment of the invention the locking device in the at least zonally or circumferentially corrugated cross-sectional area is at least zonally flexible as a result of a uniform or zonally varying wall thickness. A flexibility of the locking area is necessary for a disengagement process from the positive engaged state behind the working area. The locking device is elastically deformed, so that it is possible for the locking element or elements to slide out of the protuberance or depression of the working area. The flexibility necessary for this can either be brought about by the locking element per se or by the corrugated projection to which the locking element is fitted. The corrugated cross-section brings about an elasticity of the locking device, which on the one hand corresponds to the requirements of the discharge device during the discharge stroke and on the other, even in the case of material ageing, virtually excludes any failure of the locking device. This is in particular brought about in that, unlike in the prior art where resilient tongues made free from surrounding material are used for locking elements, a homogeneous stress distribution in the locking device is ensured. In addition, as a result of the inventive locking device design, no notched or serrated areas are required in which stress peaks could arise and which would therefore be predestined for the formation of cracks and the subsequent failure.

According to another embodiment of the invention the locking element is provided on a front face remote from the corrugated projection with a contour adapted to the geometry of the working area and which serves as a guide element for the working area. A front face of the locking element remote from the corrugated projection points with its surface normal at least approximately in the direction of the working area and comes into mechanical contact as a contact surface with a surface of the working area. As there is a relative movement between the locking device connected to the holding area and the working area during a discharge stroke of the discharge device, a low-friction and low-wear sliding process between the working area and the locking element sliding on the surface of the working area is desired. In order to bring about good sliding characteristics for this, the face of the locking element facing the working area is adapted to the working area geometry and serves as a guide element for the working area. Such an adaptation can in particular be brought about by the design of the face of the locking element as a concave or convex face, a spherical portion, a prism edge or a conical or pyramidal point. As a result of the adaptation of the face to the surface of the working area, the locking element also leads to a sliding guide of the working area. Associated with this is the limitation of the freedom of movement of the working area to a translatory movement.

According to a further embodiment of the invention the working area is provided on an outer face of the medium reservoir. This makes it possible to achieve a particularly simple construction of the discharge device, as is particularly preferred for discharge devices for single doses. For this purpose the outer face of the medium reservoir is provided with the depressions or protuberances necessary for the positive engagement of the locking device. When a force is applied by the user to the discharge device, on exceeding the operating force predetermined by the locking device a relative movement between the holding area and the working area is caused, so that the medium is discharged. A two or more times media discharge is also possible with such an arrangement. In order to ensure for this purpose a reliable, stepwise medium discharge, additional measures are necessary with regards to the design of the depressions or protuberances on the outer face of the medium reservoir.

According to another embodiment of the invention the working area is provided on an outer face of a feed sleeve, which at least zonally embraces the medium reservoir, said feed sleeve preferably has an inoperative locking area and at least one operative locking area spaced therefrom and which feed sleeve is mounted in a limited displaceable manner in the holding area and/or is controllable by a pressure sleeve and there is at least one detachable, positive pressure position between the feed sleeve and the pressure sleeve. The use of a feed sleeve leads to a decoupling of the medium reservoir from the holding area, so that a two or multiple dosing of the discharge device can be implemented in a particularly advantageous manner. During the discharge stroke the feed sleeve transfers the force applied by the user to the medium reservoir. Following the discharge of the medium quantity intended for a first dose, the feed sleeve prevents an immediate, further discharge. Thus, the user is placed in a position of performing a second and/or further discharge stroke with a clearly defined medium quantity, without it being necessary to take special precautions or pay particular attention.

The inoperative locking area of the feed sleeve is connected in an initial state of the discharge device with the locking elements of the locking device. The inoperative locking therefore brings about a dosing readiness of the discharge device and at the same time storage and transportation stability.

Through exerting an operating force on the discharge device on the part of the user, the positive connection between the inoperative locking area of the feed sleeve and the locking unit is released and permits a relative movement along the working area of the feed sleeve and the holding area. At least part of this relative movement corresponds to the first discharge stroke, which can in particular be ended by a locking of the locking device in the first operative locking area. Following said first discharge stroke, the user is able to leave the discharge device for a longer or shorter period without force application. At least one further discharge stroke can be effected by overcoming the locking forces of the operative locking area. The arrangement of the inoperative locking area and the at least one operative locking area spaced therefrom more particularly corresponds to the discharge stroke necessary for medium discharge. The pressure sleeve terminates the discharge device on a side remote from the discharge opening. A finger rest for operating the pumping device is fitted to the pressure sleeve. The pressure sleeve can be brought into the positive pressure position with the feed sleeve more particularly when the discharge device is used, which provides additional security against unintentional operation.

According to a further embodiment of the invention the pressure sleeve can be transferred from a starting locking area into at least one further pressure locking area along the feed sleeve. Through the use of the pressure sleeve for transferring the force applied by the user to the feed sleeve, it is possible to implement a multiple operation of the discharge device in the case of a constant external geometry of said device. The feed sleeve is displaced stepwise with each discharge stroke in the direction of the latter. Following a first discharge stroke and subsequent reduction of the operating force, the pressure sleeve slides from the starting locking area into the at least one pressure locking area and ensures a constant external geometry of the discharge device. Thus, for the user it is possible to bring about constant use conditions, particularly with regards to the application of operating forces.

According to a further embodiment of the invention the locking device is in the form of a corrugated and/or polygonal sleeve and in the vicinity of a first sleeve face is provided a locking element and on a further face a stiffening preferably located as a holding flange. This prevents an uncontrolled expansion of the locking device during elastic deformation when the discharge device is used. It also ensures that during advanced ageing of the locking device, the originally provided locking forces remain within a tolerance range and consequently a correct operation of the locking device is ensured.

According to a further embodiment of the invention the pressure sleeve, the feed sleeve, the locking element and the medium reservoir are so matched to one another by means of in particular positively acting locking devices that it is possible to at least perform a double discharge stroke for the discharge device. The locking devices are arranged in such a way that after performing a first discharge stroke, an intermediate position for the feed sleeve and medium reservoir is made possible whilst the pressure sleeve returns to its starting position where it assumes a new locking position with respect to the feed sleeve. Thus, at least one further discharge stroke can be carried out by the user, who moves the feed sleeve and the medium reservoir coupled thereto into the next intermediate position or an end position.

According to the invention, the problem is also solved in that the locking device in at least one plane orthogonal to a discharge stroke direction has an at least zonally or circumferentially corrugated and/or polygonal cross-section, a feed sleeve at least zonally embracing the medium reservoir being provided and which for positive locking connection with the locking device and a pressure sleeve has at least two spaced locking areas and which can be controlled by the pressure sleeve in such a way that due to an operating force applied several times by a user an at least double discharge of the medium can be effected.

Further advantages and features of the invention can be gathered from the following description of a preferred embodiment, the claims and the attached drawings, wherein show:

DETAILED DESCRIPTION OF THE DRAWINGS

Figure 1:
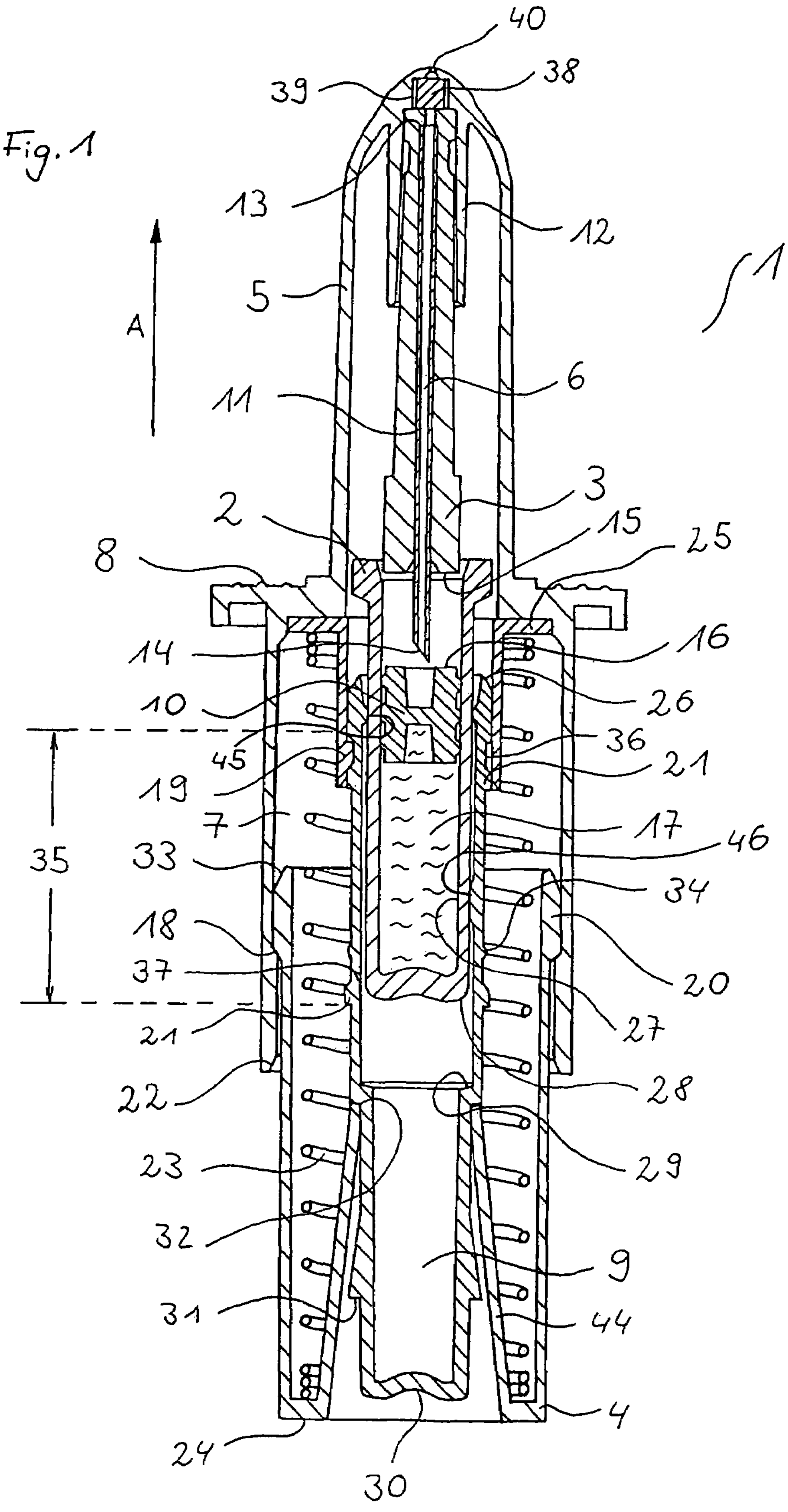
FIG. 1 A planar sectional view of a preferred embodiment of the discharge device according to the invention in an inoperative position.

A preferred embodiment of a discharge device 1 has a basic housing 5, which is constructed as a rotationally symmetrical body with a cylindrical application part rounded at the end. There is also a finger rest 8, which is connected to the application part and which is in the form of a circumferential collar. Following on to the same is provided a substantially cylindrical reception space 7, which is bounded by a circumferential, cylindrical wall.

On a side remote from the application area the reception space 7 is at least partly sealed by a pressure sleeve 4 displaceably fitted in said reception space 7. At its end directed towards the application part the pressure sleeve 4 has a stop collar 20, which has a larger external diameter than the otherwise substantially cylindrical outer contour of the pressure sleeve 4. The stop collar 20 of the pressure sleeve 4 is dimensioned in such a way that it can slide on a cylindrical inner face formed by the inner wall of the reception space 7 along a common centre axis of the reception space 7 and pressure sleeve 4. On an end of the pressure sleeve 4 facing the application part is provided a centring cone 33, which on fitting the pressure sleeve slides into the reception space 7 on an insertion bevel 22 provided there and consequently facilitates the insertion of the pressure sleeve 4. The pressure sleeve 4 is held in an inoperative position by means of a helical spring 23. It is provided at its end remote from the application part with an inwardly directed collar, which on operation of the discharge device by the user is used as a thumb support 24. The thumb support extends from a specific internal diameter as a zonally slotted pressure cone 44 in the form of a conically shaped wall in the direction of the application area.

The zonally slotted pressure cone 44 of the pressure sleeve 4 surrounds a substantially cylindrical feed sleeve 9 and is positively connected therewith on a starting locking area 32 in the form of a circumferential collar in the direction of the discharge stroke A. On applying a compressive force on the thumb support 24, the starting locking area 32 permits a force transfer from the pressure sleeve 4 to the feed sleeve 9. Counter to the discharge stroke direction A along the centre axis of the pressure sleeve and the basic housing in the direction of the application part, on said feed sleeve 9 is provided a pressure locking area 31 spaced from the starting locking area 32. The feed sleeve 9 is closed at the end remote from the application area by the feed sleeve base 30. Above the starting locking area 32 are provided on an outer contour of the feed sleeve 9 two spaced locking rings, as well as in each case a holding ring 34 spaced in the immediate vicinity from the given locking ring 21. In each case one locking ring 21 and a holding ring 34 form an inoperative locking area 36 and an operative locking area 37 of the feed sleeve 9.

The feed sleeve 9 is provided with a cylindrical bore extended over virtually the entire length and whose diameter in the vicinity of the starting locking area 32 is reduced up to just before the feed sleeve base 30. A guide nose 46 is provided on an inner wall of the feed sleeve 9 in rotationally symmetrical circular manner and displaced by 120 degrees. In addition, a circumferential guide collar 45 is provided in the end of the feed sleeve 9 facing the application area.

On the guide collar 45 and guide noses 46, during a discharge stroke, slides a medium reservoir 2 which, as a substantially cylindrical, cup-like container opened in the application area direction, is zonally surrounded by the feed sleeve 9. The medium reservoir 2 is filled with a medium 17 and closed with a sealing element 10. The sealing element 10 is made from an elastomer and is constructed as a rotationally and mirror symmetrical body and on the outer contour has several ribs acting as sealing rings. Along the symmetry axis of the sealing element 10 is in each case provided a blind bore in and counter to the axis of symmetry direction.

On a piston pressure face 16 facing the application area, during the discharge stroke, the sealing element 10 is subject to the action of a compressive force by a rod or ram pressure face 15 of a pump rod or ram 3, so that the sealing element 10 displaceably fitted in the medium reservoir 2 gives rise to a counterpressure in the stored medium 7. The pump ram 3 is guided in a ram receptacle 12 of the basic housing 5, has a substantially cylindrical and rotationally symmetrical design and has close to its axis of symmetry a medium channel 6 in the form of a medium tube 11. The medium channel 6 is closed in the direction of the application part and in the inoperative state by a valve block 38 provided in a valve chamber 39 of the basic housing 5. A discharge nozzle 40 is provided above the valve block 38 in the area surrounding an outlet of the valve chamber 39 and as a result of a significant cross-sectional difference between the diameter of the discharge nozzle 40 and the surrounding area brings about a nebulization of the discharged medium 17.

An end face of the medium tube 11 remote from the application area is cut in wedge-shaped manner and consequently forms a cutting tip 14. During the discharge stroke the cutting tip 14 slides into the bore provided in the sealing element 10 and cuts through the latter at this location. As a result the medium tube 11 can be immersed in the medium 17 stored in the medium reservoir 2.

To prevent an undesired operation of the discharge device 1, between an outer contour 35 of the feed sleeve 9 acting as a working area and a corrugated element 35, there are three locking elements 19 fitted at an angle of in each case 120 degrees in circular manner around the symmetry axis of the discharge device and which positively engage in the inoperative locking area 36 of the feed sleeve 9. In addition, there is a helical spring 23, acting as a compression spring, in the reception space 7 and in a working space formed by the pressure sleeve and presses the latter positively against a circumferential stop edge 18 formed by the outer wall of the reception space 7.

Figure 2:
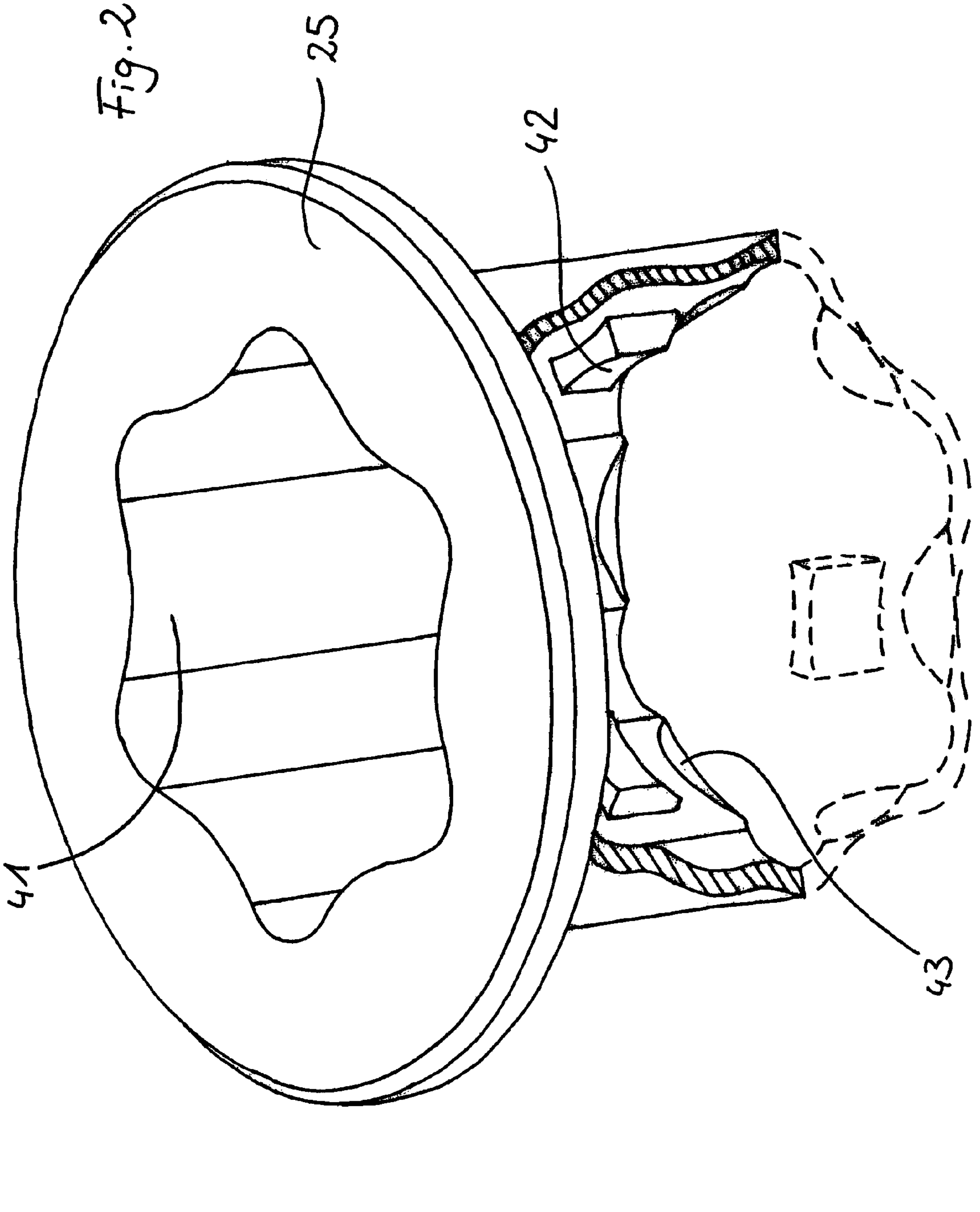
FIG. 2 A perspective, sectional representation of a a preferred embodiment of a locking device.

As can be seen in FIG. 2, the corrugated element 25 is constructed as a disk, which is broken by a contour formed from several continuously lined up arcuate segments. This contour extends over the disk thickness in the direction of a surface normal of the disk and is bounded by a thin wall. In the present embodiment, on said wall are provided locking elements 42 on three of in all six corrugated projections 41 in each case on the apex of the convexly inwardly directed projection 41 and which at the side remote from the projection 41 are adapted to the contour of the working area 35 formed by the feed sleeve 9.

Almost all the components of the discharge device 1 are manufactured by plastic injection moulding. The medium reservoir 2 is in particular made from glass or plastic. In the embodiment shown in FIG. 1, the helical spring 23 is made from metal, but by corresponding reconstruction can also be made from plastic. In the present embodiment the medium tube 11 is also made from metal, but can also be made from plastic or ceramic materials.

Following the production of the individual parts preassembly to subassemblies take place. The aim of this preassembly is for a maximum number of assembly stages to be performed by the discharge device manufacturer prior to the medium reservoir 2 being filled with medium 17. Thus, the filler of the medium 17 can carry out a rapid, inexpensive final assembly. A first subassembly comprises the basic housing 5, in which are inserted the valve block 38 and then the pump ram 3 provided with the medium channel 11. The corrugated element 25 is also inserted and fixed in the basic housing 5.

A second subassembly is formed by the pressure sleeve 4, the feed sleeve 9 and the helical spring 23. After filling the medium reservoir 2 with medium 17, the sealing element 10 is inserted and consequently the medium 17 is tightly sealed against the environment. In a further assembly stage the medium reservoir is slid into the feed sleeve 9. The first subassembly with the basic housing is then mounted, the centering cone 33 of the pressure sleeve 4 sliding along the insertion bevel 22 and after passing a constriction of the reception space 7, the positive connection between pressure sleeve 4 and basic housing 5 is made. Simultaneously the feed sleeve 9 with the inoperative locking area 36 locks positively in the locking elements 42 of the corrugated element 25 fixed to the basic housing 5. The helical spring 23 is biased and holds the pressure sleeve 4 in an inoperative position.

To bring about a medium discharge from the discharge device 1, according to FIG. 1 the user preferably places the middle and index fingers on the finger support 8, whilst simultaneously exerting a pressure on the thumb rest 24 using the thumb. The user must at least apply an actuating force which in particular consists of a biasing of the helical spring 23 and the deformation force necessary for overcoming the positive connection between the corrugated element 25 and the working area 35 of the feed sleeve 9, as well as a frictional part. As soon as the operating force is exerted by the user on the discharge device, the locking elements 19 of the corrugated element 25 are unlocked by elastic deformation of the corrugated projections 41 and allow a sliding of the working area 35 in the direction of the application area. Both the pressure sleeve 4 and the feed sleeve 9 start to move and the user only has to work against the spring tension of helical spring 23 and a sliding frictional force.

As soon as a pressure collar 29 of the feed sleeve 9 comes into contact with a medium reservoir base 28, a positive engagement is brought about there between the medium reservoir 2 and feed sleeve 9, which brings about a joint advance of these two components. Through the movement of the medium reservoir 2 in the discharge stroke direction A, the sealing element 10 comes into contact with the cutting tip 14 of the medium tube 11 and is perforated when the user exerts increasing pressure on the thumb rest 24. As a result the medium tube 11 enters the medium container 2 and the medium enclosed therein can initially flow in almost pressureless manner into the medium channel 6. A pressurizing of the medium 17 takes place during continuing movement of the medium reservoir 2 in the discharge stroke direction A. The ram pressure face 15 of the pump ram 3 engages on the piston pressure face 16 of the sealing element 10 and places the medium 17 increasingly under pressure by the thumb pressure applied by the user. As a result of the rising pressure in the medium reservoir 2, the medium 17 flows along the medium channel 6 in the direction of the valve block 38, which upwardly terminates the medium channel 6. On reaching a design-predetermined minimum pressure, the valve formed by the valve block 38 and valve block 39 opens. The medium 17 is passed into the environment in nebulized form as a result of the rapid cross-sectional change in the discharge nozzle 40.

The discharge stroke is ended as soon as the front face facing the application area of the pressure sleeve 4 strikes against the front face of the corrugated element 25. The working area 35 of the feed sleeve is designed in such a way that when the locking elements 19 of the corrugated element 25 reach such a position positively engage in the operative locking area 37 and retain the feed sleeve in this position. As a further medium flow is prevented by reaching a block length of the pressure sleeve 4, the user will reduce the thumb pressure on the thumb rest 24 and the feed sleeve base 30. Thus, the energy stored in the helical spring 23 leads to a movement of the pressure sleeve 4 counter to the discharge stroke direction A. The zonally slotted pressure cone 44 slides out of the original starting locking area 32 into the pressure locking area 31 and engages again with its stop collar 20 on the stop edge 18 of the outer sleeve of the reception space 7. This permits a further operation of the feed sleeve 9 by the pressure sleeve 4, which allows a second discharge process on applying a corresponding operating force.

In the initial phase of the discharge stroke, the operating force applied causes an internal tension in the corrugated element 25, which in the case of a corresponding design of the locking element 42 leads to an elastic deformation of the corrugated wall of the corrugated element 25, the locking elements 41 being pivotable out of their position and consequently it is possible to release the positive locking between the corrugated element 25 and the working area of the feed sleeve 9.

In another not shown embodiment the locking elements 42 are fitted to the working area 35 of the discharge device 1, the protuberances or depressions being provided for producing a positive engagement on the corrugated projections 41.

The invention claimed is:

1. Discharge device for manually producing a volume flow through a discharge stroke, comprising:

a medium reservoir for at least one medium;

a discharge opening;

a holding area;

a locking device;

a pumping device; and a working area associated with said pumping device, the working area having in an inoperative position a detachable, positive connection with a holding area via a locking device, wherein the locking device has an at least zonally corrugated cross-section in at least one plane orthogonal to a discharge stroke direction.

2. Discharge device according to claim 1, wherein the corrugated cross-section is polygonal.

3. Discharge device according to claim 1, wherein on at least one corrugated projection of the locking device facing the working area is provided a locking element.

4. Discharge device according to claim 1, wherein the locking device is at least zonally made flexible by a uniform wall thickness in the at least zonally corrugated cross-sectional area.

5. Discharge device according to claim 1, wherein the locking device is at least zonally made flexible by a sectionally varying wall thickness in the at least zonally corrugated cross-sectional area.

6. Discharge device according to claim 3, wherein the locking element has a contour adapted to the geometry of the working area, the contour is realized on a face remote from the corrugated projection and the locking element is provided as a guide element for said working area.

7. Discharge device according to claim 1, wherein the working area is provided on an outer face of the medium reservoir.

8. Discharge device according to claim 1, wherein the working area is provided on an outer face of a feed sleeve; the feed sleeve embraces the medium reservoir at least zonally and is mounted in limited displaceable manner in the holding area.

9. Discharge device according to claim 8, wherein the feed sleeve is controllable by a pressure sleeve and at least one detachable, positive pressure position is provided between the feed sleeve and the pressure sleeve.

10. Discharge device according to claim 8, wherein the feed sleeve has an inoperative locking area and at least one operative locking area spaced therefrom.

11. Discharge device according to claim 8, wherein the pressure sleeve can be transferred along the feed sleeve from a starting locking area into at least one further pressure locking area.

12. Discharge device according to claim 8, wherein the locking device is in the form of a corrugated sleeve and in the vicinity of a first sleeve face is provided at least one locking element and on a further face a stiffening preferably constructed as a holding flange.

13. Discharge device according to claim 8, wherein the locking device is in the form of a polygonal sleeve and in the vicinity of a first sleeve face is provided at least one locking element and on a further face a stiffening preferably constructed as a holding flange.

14. Discharge device according to claim 8, wherein the pressure sleeve, feed sleeve, locking element and medium reservoir are so matched to one another by means of locking devices that it is possible to at least perform a double discharge stroke of the discharge device.

15. Discharge device according to claim 14, wherein the pressure sleeve, feed sleeve, locking element and medium reservoir are matched to one another by means of positively acting locking devices.

16. Discharge device for manually producing a volume flow through a discharge stroke, comprising:

a medium reservoir for at least one medium;

a discharge opening;

a pumping device;

a holding area;

a locking device;

a feed sleeve;

a pressure sleeve;

a working area associated with said pumping device, the working area having in an inoperative position a detachable, positive connection with the holding area via the locking device, wherein the locking device has an at least zonally corrugated cross-section in at least one plane orthogonal to a discharge stroke direction, wherein the feed sleeve at least zonally embraces the medium reservoir and has at least two spaced locking areas for a positive locking connection with the locking device and the pressure sleeve, the feed sleeve being controllable by said pressure sleeve in such a way that an actuating force multiply applied by a user permits an at least double discharge of the medium.

17. Discharge device according to claim 16, wherein the locking device in at least one plane orthogonal to a discharge stroke direction has an at least zonally polygonal cross section.

* * * * *